(12) United States Patent
Wieser et al.

(10) Patent No.: US 8,252,946 B2
(45) Date of Patent: Aug. 28, 2012

(54) CRYSTALLINE FORMS OF TIGECYCLINE HYDROCHLORIDE

(75) Inventors: Josef Wieser, Polling (AT); Andreas Hotter, Woergl (AT); Arthur Pichler, Buch bei Jenbach (AT)

(73) Assignee: Sandoz AG, Basel (CH)

( * ) Notice: Subject to any disclaimer, the term of this patent is extended or adjusted under 35 U.S.C. 154(b) by 105 days.

(21) Appl. No.: 12/742,706

(22) PCT Filed: Nov. 12, 2008

(86) PCT No.: PCT/EP2008/065398
§ 371 (c)(1),
(2), (4) Date: May 13, 2010

(87) PCT Pub. No.: WO2009/062963
PCT Pub. Date: May 22, 2009

(65) Prior Publication Data
US 2011/0105772 A1     May 5, 2011

(30) Foreign Application Priority Data

Nov. 14, 2007   (EP) ..................................... 07120732

(51) Int. Cl.
*C07C 237/26* (2006.01)
(52) U.S. Cl. ..................................................... 552/205
(58) Field of Classification Search .................. None
See application file for complete search history.

(56) References Cited

U.S. PATENT DOCUMENTS

| | | | | |
|---|---|---|---|---|
| 5,675,030 A | * | 10/1997 | Krishnan et al. | 552/205 |
| 2007/0049561 A1 | * | 3/2007 | Krishnan et al. | 514/152 |
| 2008/0090789 A1 | | 4/2008 | Tsiperman et al. | |

FOREIGN PATENT DOCUMENTS

| WO | 2005056538 | 6/2005 |
|---|---|---|
| WO | 2006128150 | 11/2006 |
| WO | 2006130418 | 12/2006 |
| WO | 2006130431 | 12/2006 |
| WO | 2006130500 | 12/2006 |
| WO | 2006130501 | 12/2006 |
| WO | WO 2006/130501 | * 12/2006 |
| WO | 2007127292 | 11/2007 |
| WO | 2008066935 | 6/2008 |
| WO | 2008155405 | 12/2008 |

OTHER PUBLICATIONS

Morissette et al. in Drug Delivery Reviews, 56 (2004) 275-300.*
EU Pharmacopoeia 6.0, 1.2 (2008).
DJ. Biedenbach et al., Diagnostic Microbiology and Infectious Disease 2001 ; 40: 173-177.
PJ. Petersen et al., Antimicrob. Agents Chemoth. 2002; 46: 2595-2601.
D. Milatovic et al., Antimicrob. Agents Chemoth. 47: 400-404, (2003).
T. Hirata et al., Antimicrob. Agents Chemoth. 2004; 48: 2179-2184.
G.A. Pankey, Journal of Antimicrobial Chemotherapy 2005; 56: 470-480.
R. Harris et al., P&T 2006; 31 : 18-59.
Caira M.R., "Crystalline Polymorphism of Organic Compounds", vol. 198, Jan. 1, 1998, pp. 163-208.
International Search Report and Written Opinion issued Feb. 5, 2009 in parent PCT application.
International Preliminary Report on Patentability, (2005).
PJ. Petersen et al., Antimicrob. Agents Chemoth.1999; 43: 738-744.
R. Patel et al., Diagnostic Microbiology and Infectious Diseases 2000; 38: 177-179.
H. W. Boucher et al., Antimicrob. Agents Chemoth. 44: 2225-2229, (2000).

* cited by examiner

*Primary Examiner* — Timothy Thomas
*Assistant Examiner* — Dennis Heyer
(74) *Attorney, Agent, or Firm* — Jeffrey S. Melcher; Manelli Selter PLLC

(57) ABSTRACT

The present invention relates to crystalline forms A and B of Tigecycline hydrochloride and to methods for the preparation of the same. Furthermore the present invention relates to the use of crystalline forms A and B of Tigecycline hydrochloride as intermediates for the formulation of an anti-infective medicament. Moreover the present invention relates to pharmaceutical compositions comprising crystalline form A of Tigecycline hydrochloride in an effective amount and to the use of crystalline form A of Tigecycline hydrochloride as anti-infective medicament.

33 Claims, 6 Drawing Sheets

CRYSTALLINE FORMS OF TIGECYCLINE HYDROCHLORIDE

THE FIELD OF THE INVENTION

The present invention relates to crystalline forms A and B of Tigecycline hydrochloride and to methods for the preparation of the same. Furthermore the present invention relates to the use of crystalline forms A and B of Tigecycline hydrochloride as intermediates for the formulation of an anti-infective medicament. Moreover the present invention relates to pharmaceutical compositions comprising crystalline form A of Tigecycline hydrochloride in an effective amount and to the use of crystalline form A of Tigecycline hydrochloride as anti-infective medicament.

BACKGROUND OF THE INVENTION

Tigecycline, (4S,4aS,5aR,12aS)-4,7-Bis(dimethylamino)-9-[[[(1,1-dimethylethyl)amino]acetyl]amino]-1,4,4a,5,5a,6,11,12a-octahydro-3,10,12,12a-tetrahydroxy-1,11-dioxo-2-naphthacenecarboxamide, is a 9-t-butylglycylamido derivative of minocycline (Merck Index 14$^{th}$ Edition, monograph number 9432, CAS Registry Number 220620-09-7). Compared to other tetracycline antibiotics Tigecycline is more active against tetracycline-resistant strains and also more tolerable. Tigecycline possesses activity against bacterial isolates containing the two major determinants responsible for tetracycline-resistance: ribosomal protection and active efflux of the drug out of the bacterial cell. Furthermore Tigecycline possesses broad spectrum activity, e.g. it is active against gram-positive pathogens (e.g. methicillin-resistant *Staphylococcus aureus*, vancomycin-resistant *Enterococci*), gram-negative pathogens (e.g. *Acinetobacter baumannii*, *Stenotrophomonas maltophilia*) and anaerobic pathogens. At the moment Tigecycline is indicated for the treatment of complicated skin and soft-tissue infections and intra-abdominal infections. (P. J. Petersen et al., Antimicrob. Agents Chemoth. 1999; 43: 738-744. R. Patel et al., Diagnostic Microbiology and Infectious Disease 2000; 38: 177-179. H. W. Boucher et al., Antimicrob. Agents Chemoth. 44: 2225-2229. D. J. Biedenbach et al., Diagnostic Microbiology and Infectious Disease 2001; 40: 173-177. P. J. Petersen et al., Antimicrob. Agents Chemoth. 2002; 46: 2595-2601. D. Milatovic et al., Antimicrob. Agents Chemoth. 47: 400-404. T. Hirata et al., Antimicrob. Agents Chemoth. 2004; 48: 2179-2184. G. A. Pankey, Journal of Antimicrobial Chemotherapy 2005; 56: 470-480. R. Harris et al., P&T 2006; 31: 18-59).

U.S. Pat. No. 5,675,030 mentions a process for the preparation of Tigecycline hydrochloride by "treating" the free base with hydrochloric acid, but neither an explicit method for the preparation of crystalline Tigecycline hydrochloride, nor the existence of a crystalline form of Tigecycline hydrochloride are described. In Example 9 of said patent an aqueous solution of Tigecycline hydrochloride is lyophilized, whereas, according to U.S. Pat. No. 5,675,030, Tigecycline hydrochloride dihydrate of unknown solid state is obtained. However, repeating the experiment resulted in amorphous Tigecycline hydrochloride.

WO 2005/056538, WO 2006/130418, WO 2006/130431, WO 2006/130500 and WO 2006/130501 disclose Tigecycline, acid addition salts of Tigecycline and processes for the preparation of the same as well. However, in literature no crystalline Tigecycline hydrochloride is described.

Tigecycline is available on the market as lyophilized powder for injection, the originator is Wyeth. During the formulation process Tigecycline is first dissolved in water and then lyophilized. Therefore a crystalline form of Tigecycline or an alternative crystalline acid addition salt of Tigecycline should show high water solubility.

In 2007 the originator launched a novel formulation of Tigecycline in the US. The commercial Tygacil® 2$^{nd}$ generation product contains, according to the originator, following ingredients:

TABLE 1

Tygacil® 2$^{nd}$ generation

| INGREDIENT | QUANTITY PER VIAL |
|---|---|
| Tigecycline | 53 mg |
| Lactose monohydrate | 106 mg |
| Hydrochloric acid | Q.S. to adjust pH |
| Sodium hydroxide | Q.S. to adjust pH |
| Water for injection | Removed during lyophilization |
| Nitrogen | Q.S. |

The inventors of the present invention surprisingly found that these originator vials contain amorphous Tigecycline hydrochloride instead of the free base, which is due to the addition of hydrochloric acid for pH-adjustment. Therefore it seems to be reasonable to apply crystalline Tigecycline hydrochloride to the lyophilization process instead of the free base, as the salt shows higher water solubility than any crystalline form of the free base.

Moreover the ratio of Tigecycline to hydrochloric acid can be chosen such, that there is no need for pH-adjustment anymore.

Generally, crystalline solids have improved chemical and physical stability over the amorphous form and forms with low crystallinity, therefore crystalline Tigecycline hydrochloride is more preferred than amorphous Tigecycline hydrochloride. Thus there remains a need for crystalline Tigecycline hydrochloride with suitable solubility and stability properties for the formulation of an anti-infective medicament.

SUMMARY OF THE INVENTION

In one embodiment, the present invention refers to crystalline form A of Tigecycline hydrochloride.

Crystalline form A of Tigecycline hydrochloride can be described by an X-ray powder diffraction pattern comprising peaks at 2-theta angles of 7.6°±0.2°, 9.1±0.2°, 12.2±0.2°, 13.7±0.2°, 15.2±0.2°, 18.0±0.2°, 20.6±0.2°, 22.8±0.2° and 23.7±0.2°.

Alternatively crystalline form A of Tigecycline hydrochloride can be described by an infrared spectrum comprising peaks at wavenumbers of 3443±2 cm$^{-1}$, 3278±2 cm$^{-1}$, 2393±2 cm$^{-1}$, 1689±2 cm$^{-1}$, 1651±2 cm$^{-1}$, 1544±2 cm$^{-1}$, 1362±2 cm$^{-1}$, 1271±2 cm$^{-1}$, 1130±2 cm$^{-1}$, 1050±2 cm$^{-1}$, 871±2 cm$^{-1}$ and 808±2 cm$^{-1}$.

A first process for the preparation of crystalline form A of Tigecycline hydrochloride comprising the steps of:

a) stirring a suspension of Tigecycline in a suitable solvent at room temperature;

b) adding hydrochloric acid to the suspension;

c) isolating crystalline form A of Tigecycline hydrochloride;

is also subject matter of the present invention.

In addition a second process for the preparation of crystalline form A of Tigecycline hydrochloride, comprising the steps of:
a) dissolving Tigecycline in a suitable solvent at a temperature ranging from room temperature to the boiling point of the used solvent;
b) adding hydrochloric acid to the solution;
c) cooling down the obtained suspension to room temperature or below;
d) isolating crystalline form A of Tigecycline hydrochloride;
is subject matter of the present invention as well.

In another embodiment, the present invention refers to crystalline form B of Tigecycline hydrochloride.

Crystalline form B of Tigecycline hydrochloride can be described by an X-ray powder diffraction pattern comprising peaks at 2-theta angles of 5.8°±0.2°, 7.0±0.2°, 9.1±0.2°, 9.7±0.2°, 14.1±0.2°, 15.5±0.2°, 17.3±0.2°, 18.3±0.2°, 19.6±0.2°, 22.4±0.2°, 25.5±0.2°, 27.1±0.2° and 28.5±0.2°.

Alternatively crystalline form B of Tigecycline hydrochloride can be described by an infrared spectrum comprising peaks at wavenumbers of 3365±2 cm$^{-1}$, 3228±2 cm$^{-1}$, 1685±2 cm$^{-1}$, 1648±2 cm$^{-1}$, 1545±2 cm$^{-1}$, 1360±2 cm$^{-1}$, 1263±2 cm$^{-1}$, 1204±2 cm$^{-1}$ and 872±2 cm$^{-1}$.

A process for the preparation of crystalline form B of Tigecycline hydrochloride comprising the steps of:
a) stirring a mixture of Tigecycline and methylenehloride;
b) adding hydrochloric acid;
c) stirring the solution at room temperature or below to effect crystallization of crystalline form B of Tigecycline hydrochloride;
d) isolating crystalline form B of Tigecycline hydrochloride;
is also subject matter of the present invention.

Furthermore the present invention relates to the use of crystalline forms A and B of Tigecycline hydrochloride as intermediates for the formulation of an anti-infective medicament.

Moreover the present invention relates to pharmaceutical compositions comprising crystalline form A of Tigecycline hydrochloride in an effective amount.

In addition the present invention refers to the use of crystalline form A of Tigecycline hydrochloride as an anti-infective medicament.

Other objects, features, advantages and aspects of the present invention will become apparent to those of skill from the following description. It should be understood, however, that the description and the following specific examples, while indicating preferred embodiments of the invention, are given by way of illustration only. Various changes and modifications within the spirit and scope of the disclosed invention will become readily apparent to those skilled in the art from reading the description and from reading the other parts of the present disclosure.

DETAILED DESCRIPTION OF THE INVENTION

As used herein the term "amorphous" relates to solid material which lacks a regular crystalline structure.

The term "room temperature" as used herein indicates that the applied temperature is not critical and that no exact temperature value has to be kept. Usually, "room temperature" is understood to mean temperatures of about 15° C. to about 25° C. [see e.g. EU Pharmacopoeia 6.0, 1.2 (2008)].

The term "concentrated hydrochloric acid" relates to hydrochloric acid having a hydrochloride concentration of 37%.

The present invention relates to crystalline forms A and B of Tigecycline hydrochloride and to processes for the preparation thereof.

The chemical structure of Tigecycline hydrochloride is shown in FIG. A.

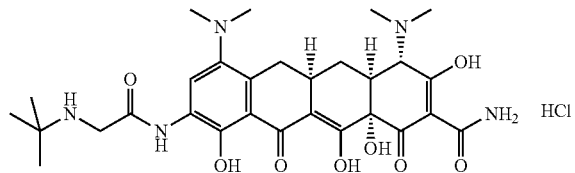

FIG. A: Chemical Structure of Tigecycline Hydrochloride

The crystalline forms A and B of Tigecycline hydrochloride may be characterized e.g. by a typical X-ray powder diffraction pattern, an infrared spectrum or a differential scanning calorimetric curve. Each of these characteristics on its own is sufficient to unambiguously define and identify the crystalline form of Tigecycline hydrochloride but they also may be combined with each other.

The present invention relates to crystalline form A of Tigecycline hydrochloride characterized by an X-ray powder diffraction pattern with peaks at 2-theta angles of 7.6°±0.2°, 9.1±0.2°, 12.2±0.2°, 13.7±0.2°, 15.2±0.2°, 18.0±0.2°, 20.6±0.2°, 22.8±0.2° and 23.7±0.2°. A characteristic X-ray powder diffraction pattern of crystalline form A of Tigecycline hydrochloride is shown in FIG. 1 and some characteristic peaks are listed in Table 2.

Figure 1:
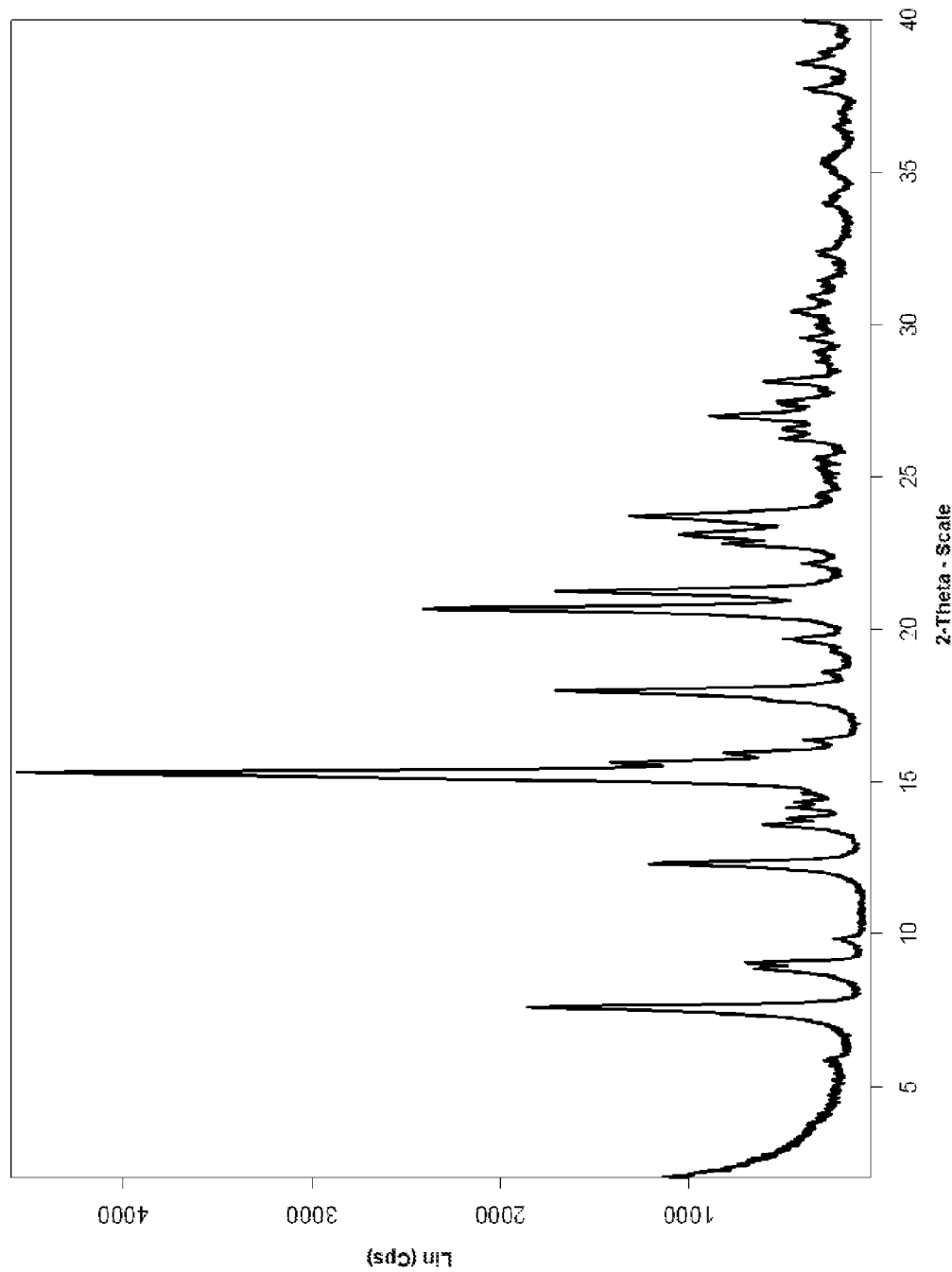
FIG. 1: X-ray powder diffraction pattern of crystalline form A of Tigecycline hydrochloride

Accordingly, in a preferred embodiment, the present invention relates to crystalline form A of Tigecycline hydrochloride characterized by an X-ray powder diffraction pattern substantially in accordance with Table 2 and FIG. 1.

TABLE 2

Characteristic X-Ray Powder Diffraction (XRPD) peaks of crystalline form A of Tigecycline hydrochloride

| ANGLE [°2-THETA] | RELATIVE INTENSITY [%] |
|---|---|
| 7.6 | 41.5 |
| 9.1 | 58.1 |
| 12.2 | 27.2 |
| 13.7 | 37.3 |
| 15.2 | 92.3 |
| 18.0 | 81.6 |
| 20.6 | 100.0 |
| 22.8 | 42.3 |
| 23.7 | 41.1 |

Figure 2:
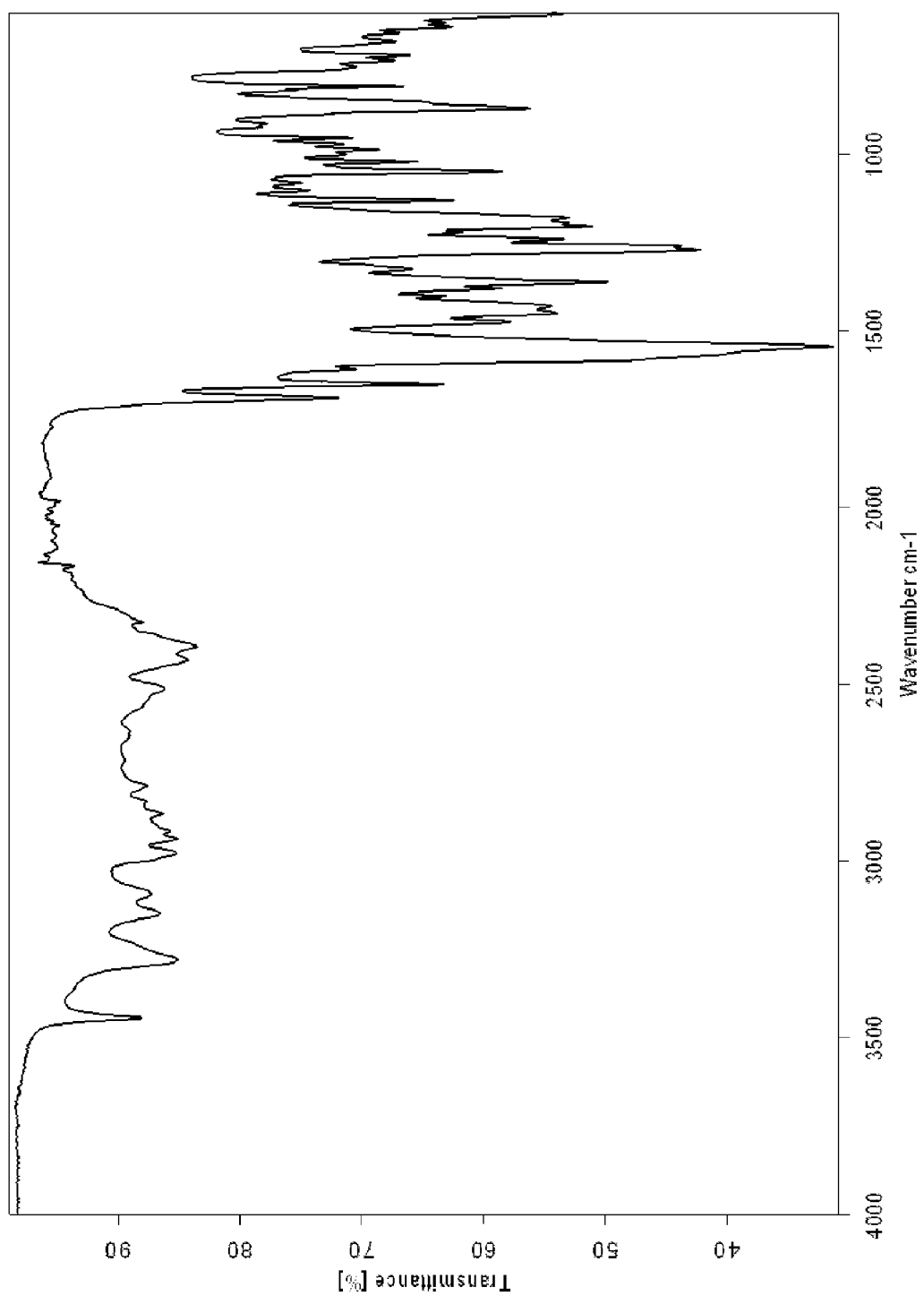
FIG. 2: Infrared spectrum of crystalline form A of Tigecycline hydrochloride

Crystalline form A of Tigecycline hydrochloride also may be characterized by a typical infrared spectrum as shown in FIG. 2. Accordingly in a further preferred embodiment, the present invention relates to crystalline form A of Tigecycline hydrochloride characterized by an infrared spectrum substantially in accordance with FIG. 2. Characteristic bands are present at wavenumbers of $3443\pm2$ cm$^{-1}$, $3278\pm2$ cm$^{-1}$, $2393\pm2$ cm$^{-1}$, $1689\pm2$ cm$^{-1}$, $1651\pm2$ cm$^{-1}$, $1544\pm2$ cm$^{-1}$, $1362\pm2$ cm$^{-1}$, $1271\pm2$ cm$^{-1}$, $1130\pm2$ cm$^{-1}$, $1050\pm2$ cm$^{-1}$, $871\pm2$ cm$^{-1}$ and $808\pm2$ cm$^{-1}$.

Figure 3:
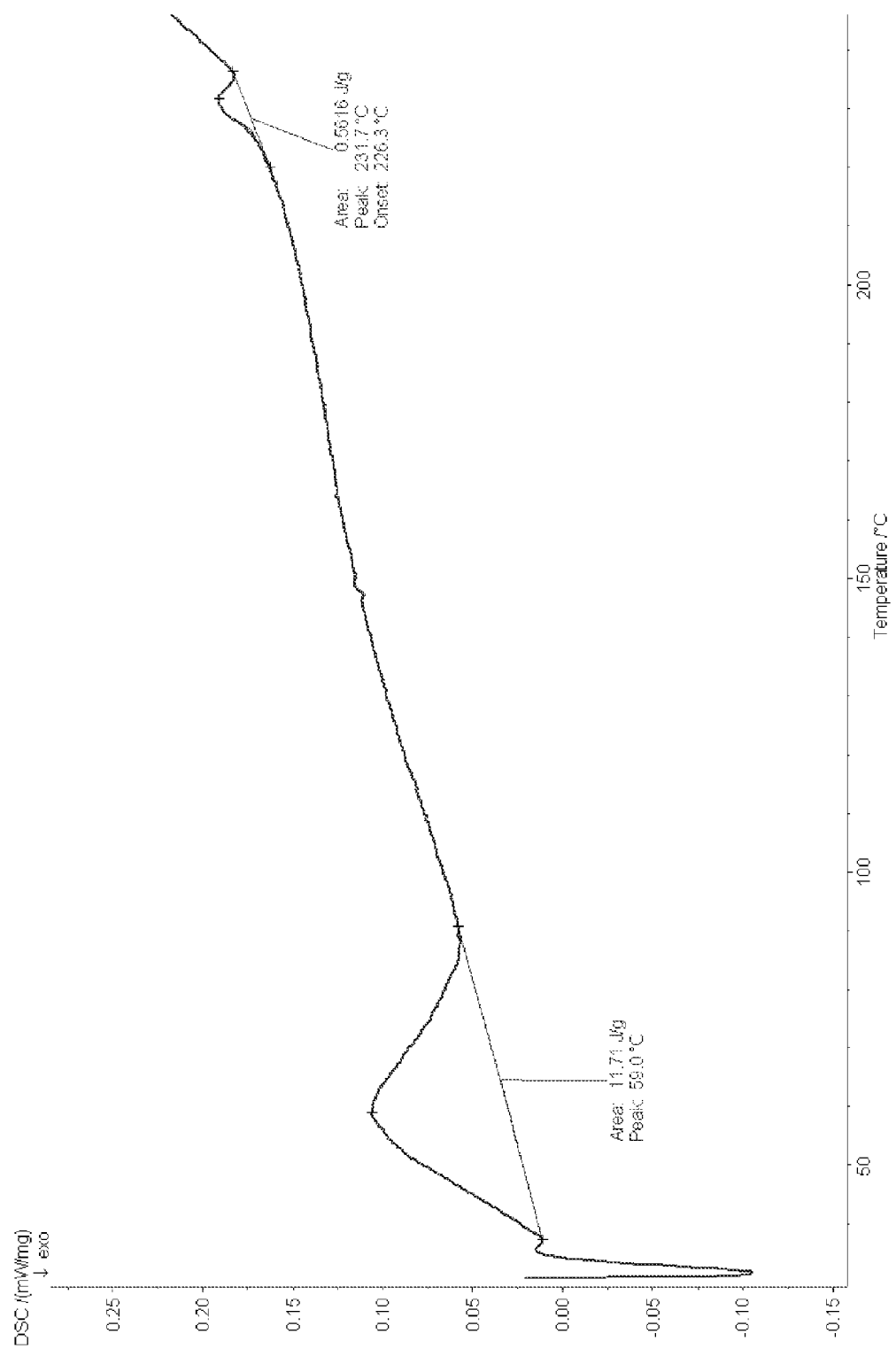
FIG. 3: Differential Scanning calorimetric curve of crystalline form A of Tigecycline hydrochloride

In addition crystalline form A of Tigecycline hydrochloride may be characterized by a typical differential scanning calorimetric curve as shown in FIG. 3. The curve displays a first endothermic peak with a maximum at about 59° C., which may be due to desolvation. The second endothermic peak with a maximum at about 232° C. may be due to the melting process. Compared to the melting points of the crystalline forms I to V disclosed in WO 2006/128150, which range from 167° C. to 174° C. a melting point of 232° C. proves high thermal stability.

Accordingly in another preferred embodiment the present invention relates to crystalline form A of Tigecycline hydrochloride characterized by a differential scanning calorimetric curve substantially in accordance with FIG. 3.

In one embodiment, the present invention provides a first process for the preparation of crystalline form A of Tigecycline hydrochloride, comprising the steps of:
   a) stirring a suspension of Tigecycline in a suitable solvent at room temperature;
   b) adding hydrochloric acid to the suspension;
   c) isolating crystalline form A of Tigecycline hydrochloride;

In another embodiment, the present invention provides a second process for the preparation of crystalline form A of Tigecycline hydrochloride, comprising the steps of:
   a) dissolving Tigecycline in a suitable solvent at a temperature ranging from room temperature to the boiling point of the used solvent;
   b) adding hydrochloric acid to the solution;
   c) cooling down the obtained suspension to room temperature or below;
   d) isolating crystalline form A of Tigecycline hydrochloride;

Any form of Tigecycline may be used in step a) of the above processes, e.g. amorphous forms, crystalline forms, mixtures of amorphous and crystalline forms, mixtures of different crystalline forms, hydrates or solvates. Suitable crystalline forms may be forms I to V of WO 2006/128150, forms I and II of WO 2007/127292 or mixtures thereof.

The concentration of Tigecycline in step a) of the above processes depends on the form of Tigecycline and on the solvent used. Generally the second process asks for lower concentrations than the first, because prior to the acid addition Tigecycline is completely dissolved. In the first process Tigecycline preferably is used at a concentration ranging from 5 to 200 g/L, more preferably from 10 to 50 g/L. Concentrations preferably ranging from 5 to 50 g/L, most preferably from 5 to 15 g/L are applied in the second process.

The temperature in step a) of the above second process may vary. However, the temperature is chosen such that at a given concentration of a particular form of Tigecycline in a particular solvent a clear solution is obtained. Therefore it may become necessary to heat the solvent to reflux.

Suitable solvents in step a) of the above processes are for example ketones such as acetone or ethylmethylketone, nitriles such as acetonitrile, esters such as methylacetate, ethylacetate and isopropylacetate and ethers such as tetrahydrofuran and 1,4-dioxane. Also suitable are mixtures of polar and apolar solvents such as dimethylformamid/diethylether. Preferably the solvent is chosen from acetone or acetonitrile, most preferably the solvent is acetonitrile.

Any suitable hydrochloric acid may be used in step b) of the above described processes. Either diluted or concentrated hydrochloric acid having a concentration ranging from 3 to 38% can be employed. Preferably hydrochloric acid having a concentration of about 10 to 37%, most preferably having a concentration of about 18% is used.

The ratio of Tigecycline to hydrochloric acid used may vary. Typically about 0.9 to about 1.5 equivalents, most preferably 1.0 to 1.4 equivalents of hydrochloric acid to 1 equivalent Tigecycline (mol:mol) will be employed. However, the ratio should be chosen such that no free base is present anymore ($\geq 1.0$ mol equivalent HCl in crystal structure) and that the amount of undesired byproducts is as low as possible. In addition the ratio also depends on the concentration of the hydrochloric acid used. For example when using concentrated hydrochloric acid, 1.1 mol equivalent are preferably used, when using 5 N hydrochloric acid, 1.0 equivalent hydrochloric acid is preferably used in order to find at least 1.0 mol equivalent HCl in the crystal lattice of Tigecycline hydrochloride and keeping undesired by products under an acceptable limit. Table 3 shows the amount of hydrochloride in the crystal structure of Tigecycline hydrochloride and the undesired byproducts found in dependence on the amount and concentration of hydrochloric acid used. The inventors found 0.9 to 1.4 mol equivalents HCl in the crystal lattice, therefore form A is a monohydrochloride.

TABLE 3

Varying amounts of HCl and of undesired byproducts depending on the amount and concentration of hydrochloric acid applied

| HCL$_{CONC.}$(37%) USED [MOL EQUIVALENT] | 5N HCL USED [MOL EQUIVALENT] | HCL FOUND [MOL EQUIVALENT] | 4-EPI-TIGECYCLINE [AREA %] | TOTAL IMPURITIES [AREA %] |
|---|---|---|---|---|
| 1.0 | | 0.9 | 0.08 | 0.52 |
| 1.1 | | 1.0 | 0.09 | 0.45 |
| 1.2 | | 1.1 | 0.20 | 0.53 |
| 1.3 | | 1.2 | 0.54 | 1.09 |
| 1.4 | | 1.2 | 0.37 | 0.69 |
| 1.5 | | 1.4 | 1.02 | 1.35 |
| | 1.0 | 1.1 | 0.15 | 0.50 |
| | 1.1 | 1.2 | 0.18 | 0.51 |

The above mentioned processes represent straight forward processes for preparing crystalline Tigecycline hydrochloride form A in a simple and fast manner suitable for pharmaceutical scale-up. Form A of Tigecycline hydrochloride is also a particularly suitable form for the isolation of Tigecycline hydrochloride in the last step of the synthesis.

The water content of crystalline form A of Tigecycline hydrochloride may vary from about 0-6.0% e.g. the water content is 0% when stored at 1.7% relative humidity at 25° C., 2.7% when stored at 42.7% relative humidity at 25° C. and 5.8% when stored at 80% relative humidity at 25° C.

Tigecycline hydrochloride form A crystallizes in small ellipsoidal needles and columns having a length ranging from about 5-20 μm.

Furthermore the present invention relates to crystalline form B of Tigecycline hydrochloride characterized by an X-ray powder diffraction pattern with peaks at 2-theta angles of 5.8°±0.2°, 7.0±0.2°, 9.1±0.2°, 9.7±0.2°, 14.1±0.2°, 15.5±0.2°, 17.3±0.2°, 18.3±0.2°, 19.6±0.2°, 22.4±0.2°, 25.5±0.2°, 27.1±0.2° and 28.5±0.2°. A characteristic X-ray powder diffraction pattern of crystalline form B of Tigecycline hydrochloride is shown in FIG. 4 and some characteristic peaks are listed in Table 4.

Figure 4:
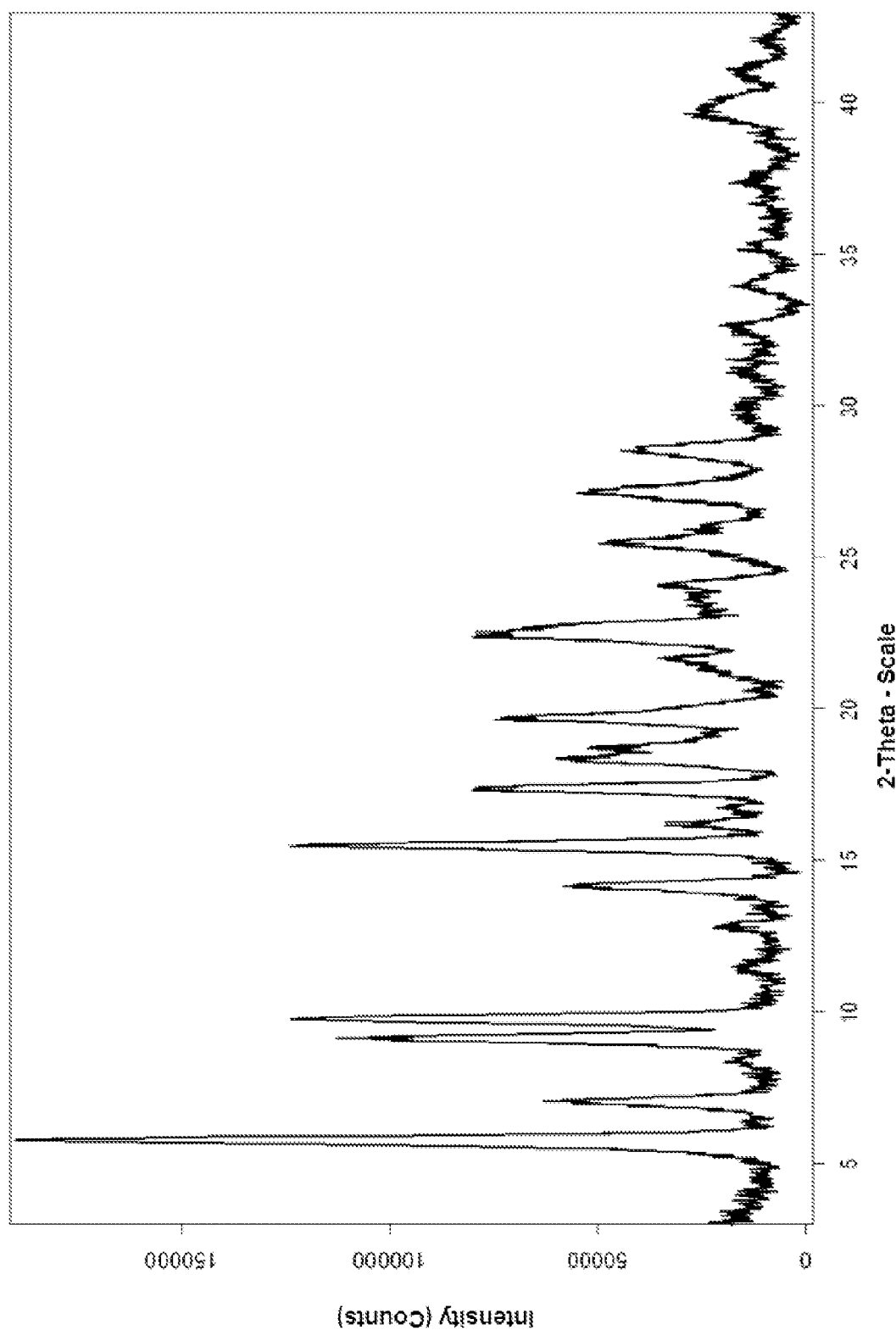
FIG. 4: X-ray powder diffraction pattern of crystalline form B of Tigecycline hydrochloride

Accordingly, in a preferred embodiment, the present invention relates to crystalline form B of Tigecycline hydrochloride characterized by an X-ray powder diffraction pattern substantially in accordance with Table 4 and FIG. 4.

TABLE 4

Characteristic X-Ray Powder Diffraction (XRPD) peaks of crystalline form B of Tigecycline hydrochloride

| ANGLE [°2-THETA] | RELATIVE INTENSITY [%] |
|---|---|
| 5.8 | 100.0 |
| 7.0 | 33.0 |
| 9.1 | 59.2 |
| 9.7 | 64.9 |
| 14.1 | 30.6 |
| 15.5 | 65.1 |
| 17.3 | 42.2 |
| 18.3 | 31.5 |
| 19.6 | 39.4 |
| 22.4 | 42.1 |
| 25.5 | 26.2 |
| 27.1 | 28.8 |
| 28.5 | 23.4 |

Figure 5:
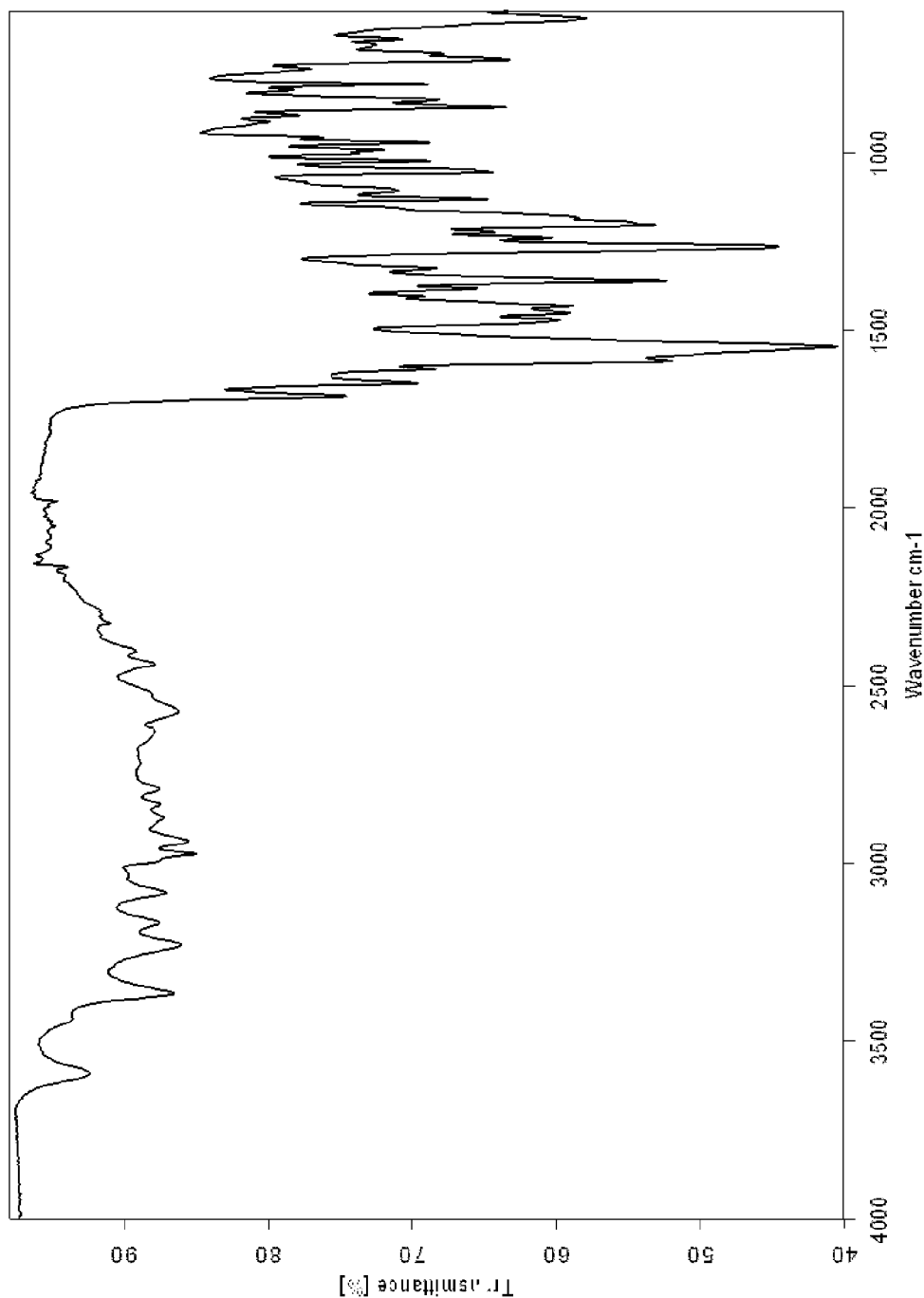
FIG. 5: Infrared spectrum of crystalline form B of Tigecycline hydrochloride

Crystalline form B of Tigecycline hydrochloride also may be characterized by a typical infrared spectrum as shown in FIG. 5. Accordingly in a further preferred embodiment, the present invention relates to crystalline form B of Tigecycline hydrochloride characterized by an infrared spectrum substantially in accordance with FIG. 5. Characteristic bands are present at wavenumbers of 3365±2 cm$^{-1}$, 3228±2 cm$^{-1}$, 1685±2 cm$^{-1}$, 1648±2 cm$^{-1}$, 1545±2 cm$^{-1}$, 1360±2 cm$^{-1}$, 1263±2 cm$^{-1}$, 1204±2 cm$^{-1}$ and 872±2 cm$^{-1}$.

Figure 6:
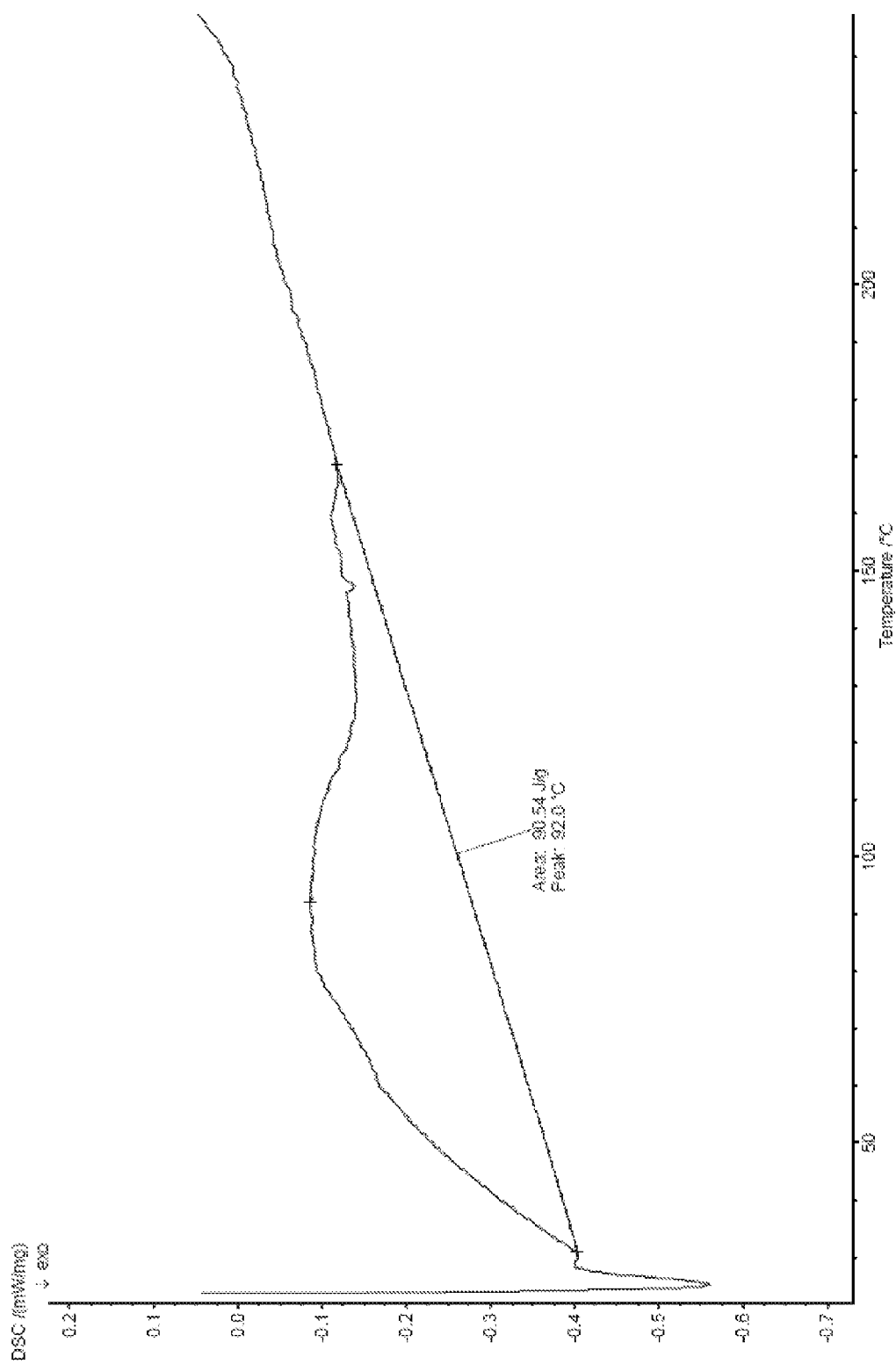
FIG. 6: Differential Scanning calorimetric curve of crystalline form B of Tigecycline hydrochloride

The DSC curve in FIG. 6 shows a broad endotherm from the beginning of the measurement until about 170° C. with a maximum at about 92° C. This peak may be due to desolvation.

In one embodiment, the present invention provides a process for the preparation of crystalline form B of Tigecycline hydrochloride, comprising the steps of:
 a) stirring a mixture of Tigecycline and methylenehloride;
 b) adding hydrochloric acid;
 c) stirring the solution at room temperature or below to effect crystallization of crystalline form B of Tigecycline hydrochloride;
 d) isolating crystalline form B of Tigecycline hydrochloride;

Any form of Tigecycline may be used in step a) of the above process, e.g. amorphous forms, crystalline forms, mixtures of amorphous and crystalline forms, mixtures of different crystalline forms, hydrates or solvates. Suitable crystalline forms may be forms I to V of WO 2006/128150, forms I and II of WO 2007/127292 or mixtures thereof.

The concentration of Tigecycline in step a) of the above process depends on the form of Tigecycline used. Tigecycline preferably is used at a concentration ranging from 5 to 100 g/L, more preferably from 5 to 50 g/L and most preferably the concentration ranges from 5 g/L to 15 g/L.

Surprisingly crystalline form B of Tigecycline hydrochloride does only crystallize from methylenchloride. When using other solvents, like for example alcohols such as ethanol, isopropanol or 2-butanol, ketones such as acetone or ethylmethylketone, nitriles such as acetonitrile, esters such as methylacetate, ethylacetate and isopropylacetate or ethers such as tetrahydrofuran and 1,4-dioxane crystalline form B of Tigecycline hydrochloride does not crystallize. The inventors of the present invention found out that the methylenechloride content of crystalline form B of Tigecycline hydrochloride ranges from 0.4 to 0.5 mol (analyzed by GC, Table 5).

Any suitable hydrochloric acid can be used in step b) of the above described process. Either diluted or concentrated hydrochloric acid having a concentration in the range from 3 to 38% can be employed. Preferably hydrochloric acid having a concentration of about 10 to 37%, most preferably having a concentration of about 18% is used.

The ratio of Tigecycline to hydrochloric acid used may vary. Typically about 0.9 to about 1.5 equivalents, most preferably 1.0 to 1.4 equivalents of hydrochloric acid to 1 equivalent Tigecycline (mol:mol) will be employed. Table 5 displays that the amount of hydrochloride in the crystal lattice is 1.0 mol equivalent no matter if 1.0 or 1.4 mol equivalent hydrochloric acid are used. Therefore crystalline form B of Tigecycline hydrochloride is a monohydrochloride.

TABLE 5

Varying amounts of HCl, methylenchloride and undesired byproducts depending on the amount of hydrochloric acid applied

| 5N HCL USED [MOL EQUIVALENT] | HCL FOUND [MOL EQUIVALENT] | 4-EPI-TIGECYCLINE [AREA %] | TOTAL IMPURITIES [AREA %] | METHYLENCHLORIDE FOUND [MOL EQUIVALENT] |
|---|---|---|---|---|
| 1.0 | 1.0 | 1.20 | 2.41 | 0.5 |
| 1.1 | 1.0 | 1.81 | 2.99 | 0.5 |
| 1.3 | 1.0 | 1.73 | 2.97 | 0.4 |
| 1.4 | 1.0 | 1.06 | 2.20 | 0.5 |

The crystalline form B of Tigecycline hydrochloride crystallizes in small needles having a length ranging from about 10-15 μm.

The finished dosage form contains lyophilized amorphous Tigecycline respectively Tigecycline hydrochloride. Before lyophilizing, Tigecycline respectively Tigecycline hydrochloride is dissolved in water, thus water solubility is an important factor to consider. Table 6 displays the solubility data of the different crystalline forms of Tigecycline free base compared with these of crystalline forms A and B of Tigecycline hydrochloride.

Crystalline form A of Tigecycline hydrochloride clearly shows the highest water solubility. For example crystalline form A shows higher water solubility than forms I, II, III, IV and V of WO 2006/128150 and also higher water solubility than crystalline forms I and II of WO 2007/127292. On the other hand form B of Tigecycline hydrochloride shows lower solubility than form A. Nevertheless form B nearly shows the same water solubility as the most soluble free base, namely form IV of WO 2006/128150. Consequently the crystalline forms of Tigecycline hydrochloride of the present invention, especially form A, are particularly suitable forms for the lyophilization process in order to formulate an anti-infective medicament.

TABLE 6

Water solubility of different crystalline forms of Tigecycline and Tigecycline hydrochloride

| FORM | CONCENTRATION [MG/ML] | BASE USED [MG BASE EQUIVALENT] |
|---|---|---|
| WO 2006/128150 (Free base) | | |
| I | 201 | 206 |
| II | 170 | 280 |
| III | 174 | 198 |
| IV | 322 | 387 |
| V | 134 | 180 |
| WO 2007/127292 (Free base) | | |
| I | 54 | 156 |
| II | 76 | 198 |
| Present invention (Hydrochloride) | | |
| A | 503 | 621 |
| B | 323 | 332 |

The crystalline forms of Tigecycline hydrochloride of the present invention represent thermodynamically stable forms, which means they do not convert into other crystalline or amorphous forms when storing them even at elevated temperatures. For example the crystalline forms A and B of Tigecycline hydrochloride of the present invention did not convert into other crystalline or amorphous forms after storing for 7 days at 80° C.

Tigecycline must be available in a physical stable form as well, in order to avoid degradation and as a consequence the building of undesired byproducts. Table 7 displays the stability data of the different crystalline forms of Tigecycline free base compared with the stability data of the crystalline forms of Tigecycline hydrochloride from the present invention. After storing for 7 days at 80° C. one can see that forms I and II of WO 2006/128150 show a tremendous increase in total impurities. All the other crystalline forms of Tigecycline respectively Tigecycline hydrochloride which have been tested showed satisfying stability data when considering that 7 days at 80° C. are extreme conditions, which an active pharmaceutical ingredient will never experience in his lifecycle under ordinary circumstances. For example the 4-Epi-Tigecycline content of crystalline form A of Tigecycline hydrochloride practically did not change and also the increase of total impurities was low.

TABLE 7

Thermal stability of crystalline forms of Tigecycline respectively Tigecycline hydrochloride

| FORM | 4-EPI-TIGECYCLINE AT AMBIENT CONDITIONS | 4-EPI-TIGECYCLINE 7 DAYS AT 80° C. | TOTAL IMPURITIES AT AMBIENT CONDITIONS | TOTAL IMPURITIES 7 DAYS AT 80° C. |
|---|---|---|---|---|
| WO2006/128150 (free base) | | | | |
| I | 0.36 | 2.15 | 0.75 | 11.20 |
| II | 1.04 | 10.83 | 1.60 | 18.44 |
| III | 0.16 | 2.18 | 0.16 | 4.46 |
| IV | 0.23 | 0.38 | 0.40 | 0.87 |
| V | <0.05 | 0.18 | 0.22 | 0.37 |
| WO2007/127792 (free base) | | | | |
| I | 0.34 | 1.26 | 0.59 | 2.22 |
| II | 0.17 | 0.38 | 0.24 | 0.91 |
| Present invention (Hydrochloride) | | | | |
| A | 0.84 | 0.89 | 1.07 | 1.81 |
| B | 0.93 | 1.60 | 1.91 | 4.19 |

Moreover crystalline forms A and B of Tigecycline hydrochloride of the present invention show better physical stability than amorphous Tigecycline hydrochloride. For example amorphous Tigecycline hydrochloride was prepared by lyophilization and stored for about 9 months at room temperature. The batch showed a 4-Epi-Tigecycline content of 19.56% and 21.55% total impurities. Therefore amorphous Tigecycline hydrochloride is not suitable as an intermediate for the formulation of an anti-infective medicament, due to the low stability.

To sum it up, crystalline forms A and B of Tigecycline hydrochloride, especially form A, possess excellent water solubility and good physical and thermodynamical stability and are therefore suitable intermediates for the formulation of an anti-infective medicament.

Water solubility is an important factor to consider as Tigecycline respectively Tigecycline hydrochloride is dissolved in water before lyophilization during the formulation process. That's why the crystalline forms of the present invention, especially form A which shows the highest water solubility, are particularly suitable intermediates for the formulation of an anti-infective medicament.

In addition the thermodynamical and physical stabilities of the crystalline forms of the present invention were satisfying as well. The two crystalline forms of the present invention neither showed a noticeable increase in impurities nor a conversion of the crystal structure after storing at extreme conditions.

The novel crystalline form A of Tigecycline hydrochloride of the present invention may be used alone as antibacterial drug or in the form of a suitable pharmaceutical composition containing the novel form. In addition the present invention relates to the use of crystalline form A of Tigecycline hydrochloride as an anti-infective medicament.

The novel forms A and B of Tigecycline hydrochloride are particularly useful for the treatment of infections. Therefore, the present invention relates to the use of crystalline forms A and B of Tigecycline hydrochloride as intermediates for the formulation of an anti-infective medicament.

Moreover the present invention relates to pharmaceutical compositions comprising an effective amount of crystalline form A of Tigecycline hydrochloride.

The invention is further described by reference to the following examples. These examples are provided for illustration purposes only and are not intended to be limiting the present invention in any way.

EXAMPLES

X-ray powder diffraction pattern (XRPD) were collected on a Unisantis XMD 300 X-ray powder diffractometer with a position sensitive detector in parallel beam optics using the following acquisition conditions: tube anode: Cu, 40 kV, 0.8 mA; 3-43° theta/2αeta; simultaneous detection of regions of 10° per step with detector resolution 1024, counting time 300 seconds per step. Samples were measured at room temperature in a standard sample holder on a rotating sample spinner. A typical precision of the 2-theta values is in the range of ±about 0.2° 2-Theta. Thus a diffraction peak that appears at 5.0° 2-theta can appear between 4.8° and 5.2° 2-theta on most X-ray diffractometers under standard conditions.

Infrared spectra (IR) were collected on a MKII Golden Gate™ Single Reflection Diamond ATR (attenuated total reflection) cell with a Bruker Tensor 27 FTIR spectrometer with 4 $cm^{-1}$ resolution at ambient conditions. To collect a spectrum a spatula tip of a sample was applied to the surface of the diamond in powder form. Then the sample was pressed onto the diamond with a sapphire anvil and the spectrum was recorded. A spectrum of the clean diamond was used as background spectrum. A typical precision of the wavenumber values is in the range of about ±2 $cm^{-1}$. Thus, an infrared peak that appears at 1716 $cm^{-1}$ can appear between 1714 and 1718 $cm^{-1}$ on most infrared spectrometers under standard conditions.

Differential scanning calorimetry (DSC) was performed on a Netzsch DSC 204. About 4 mg sample was heated in 25 μl Al-Pans with loose lids from room temperature to 250° C. at a rate of 10° C./min. Nitrogen (purge rate 20 ml/min) was used as purge gas.

Example 1

Preparation of Crystalline Form a of Tigecycline Hydrochloride

A suspension of Tigecycline was prepared by mixing a solid Tigecycline sample and acetonitrile in amounts as shown in Table A. The mixture was than stirred for 1 hour at room temperature before 5 N hydrochloric acid was added in amounts corresponding to Table A. After stirring for about 20 hours the solid was filtered off and dried at room temperature under vacuum to obtain crystalline form A of Tigecycline hydrochloride.

TABLE A

| | TIGE-CYCLINE [MG] | ACETO-NITRILE [ML] | HCL [MOL EQUIVALENTS] | FORM | YIELD [%] | HPLC-PURITY [AREA %] |
|---|---|---|---|---|---|---|
| a | 500 | 12 | 1.0 | A | 100 | 99.50 |
| b | 1000 | 24 | 1.1 | A | 101 | 99.46 |

Example 2

Preparation of Crystalline Form a of Tigecycline Hydrochloride

A suspension of Tigecycline was prepared by mixing a solid Tigecycline sample and acetonitrile in amounts as shown in Table B. The mixture was than stirred for about 1 hour at room temperature before concentrated hydrochloric acid was added in amounts corresponding to Table B. After stirring for about 4 hours the solid was filtered off and dried at room temperature under vacuum to obtain crystalline form A of Tigecycline hydrochloride.

TABLE B

| | TIGE-CYCLINE [MG] | ACETO-NITRILE [ML] | HCL [MOL EQUIVALENTS] | FORM | YIELD [%] | HPLC-PURITY [AREA %] |
|---|---|---|---|---|---|---|
| a | 2500 | 60 | 1.0 | A | 94 | 99.48 |
| b | 1000 | 24 | 1.1 | A | 88 | 99.55 |
| c | 1000 | 24 | 1.2 | A | 101 | 99.47 |
| d | 3000 | 72 | 1.3 | A | 102 | 98.91 |
| e | 1000 | 24 | 1.4 | A | 100 | 99.31 |
| f | 500 | 12 | 1.5 | A | 94 | 98.65 |

Example 3

Preparation of Crystalline Form a of Tigecycline Hydrochloride

A solution of Tigecycline was prepared by mixing 500 mg of a solid Tigecycline sample with 10 ml acetone. Within about 5 minutes a precipitate appeared and the suspension was further stirred for 1.75 h. 143 μl (1.0 mol equivalent) 5N hydrochloric acid were added to the suspension and stirring was continued for 5 hours. Finally the solid was filtered off, washed with acetone and dried at room temperature under vacuum to obtain 440 mg (97% yield) of crystalline form A of Tigecycline hydrochloride (98.73% purity by HPLC).

Example 4

Preparation of Crystalline Form a of Tigecycline Hydrochloride 50.0 mg Tigecycline (Tygacil® 50 mg, Wyeth, powder for infusion) were dissolved in 1 ml acetone and the solution was stirred at room temperature. After about one minute an orange precipitate appeared (form VI). Afterwards 8.4 mg (1 eq) concentrated hydrochloric acid were added and the suspension was stirred at room temperature. The colour of the suspension changed after about 5 minutes from orange to yellow and the suspension was stirred for 2.5 hours at room temperature. The solid was filtered off, washed with acetone and dried under vacuum at room temperature to obtain 51.8 mg (98% yield) of crystalline form A of Tigecycline hydrochloride.

Example 5

Preparation of Crystalline Form a of Tigecycline Hydrochloride 50.0 mg Tigecycline (Tygacil® 50 mg, Wyeth®, powder for infusion) were dissolved in 500 μl ethylmethylketone and the solution was stirred at room temperature. After about one minute an orange precipitate appeared (essentially pure form III). Afterwards 8.4 mg (1 eq) concentrated hydrochloric acid were added and the suspension was stirred for approximately 3 hours. The solid was filtered off, washed with ethylmethylketone and dried under vacuum at room temperature to obtain 43.7 mg (82% yield) of crystalline form A of Tigecycline hydrochloride.

Example 6

Preparation of Crystalline Form B of Tigecycline Hydrochloride

A suspension of Tigecycline was prepared by mixing a solid Tigecycline sample and methylenchloride in amounts as shown in Table C. The mixture was than stirred at room temperature and 5N hydrochloric acid was added in amounts corresponding to Table C. After stirring for about 92 hours the solid was filtered off and dried at room temperature under vacuum to obtain crystalline form B of Tigecycline hydrochloride.

TABLE C

|   | TIGECYCLINE [MG] | ACETONITRILE [ML] | HCL [MOL EQUIVALENTS] | FORM | YIELD [%] | HPLC-PURITY [AREA %] |
|---|---|---|---|---|---|---|
| a | 500 | 6 | 1.0 | B | 61 | 97.59 |
| b | 500 | 6 | 1.1 | B | 68 | 97.01 |
| c | 500 | 6 | 1.3 | B | 33 | 97.03 |
| d | 500 | 6 | 1.4 | B | 36 | 97.80 |

Example 7

Water Solubility Testing

A UV-vis Lambda 35 spectrophotometer (Perkin-Elmer) was used (λ=347 nm, 1.0 cm quartz cells). Perkin Elmer® UV Win Lab-5.1 software was used.

A saturated solution of Tigecycline respectively Tigecycline hydrochloride in distilled water was prepared and the suspension was stirred at room temperature for 30 minutes with a stirring speed of 1000 U/min. The suspension was filtrated through a 0.45 μm filter. Finally the resulting solution was diluted 10000-fold and measured against water at a wavelength of 347 nm.

The invention claimed is:

1. A crystalline form A of Tigecycline hydrochloride having an X-ray powder diffraction pattern with peaks at 2-theta angles of 7.6°±0.2°, 9.1±0.2°, 12.2±0.2°, 13.7±0.2°, 15.2±0.2°, 18.0±0.2°, 20.6±0.2°, 22.8±0.2° and 23.7±0.2°.

2. The crystalline form A of Tigecycline hydrochloride according to claim 1, having an X-ray powder diffraction pattern of FIG. 1.

3. The crystalline form A of Tigecycline hydrochloride according to claim 1, having an Infrared spectrum with peaks at wavenumbers of 3443±2 $cm^{-1}$, 3278±2 $cm^{-1}$, 2393±2 $cm^{-1}$, 1689±2 $cm^{-1}$, 1651±2 $cm^{-1}$, 1544±2 $cm^{-1}$, 1362±2 $cm^{-1}$, 1271±2 $cm^{-1}$, 1130±2 $cm^{-1}$, 1050±2 $cm^{-1}$, 871±2 $cm^{-1}$ and 808±2 $cm^{-1}$.

4. The crystalline form A of Tigecycline hydrochloride according to claim 1, having an Infrared spectrum of FIG. 2.

5. The crystalline form A of Tigecycline hydrochloride according to claim 1, having a differential scanning calorimetric curve having two endothermic peaks with maxima at about 59° C. and 232° C., when heated at a rate of 10° C. per minute.

6. The crystalline form A of Tigecycline hydrochloride according to claim 1, having a differential scanning calorimetric curve of FIG. 3.

7. A process for the preparation of crystalline form A of Tigecycline hydrochloride as defined in claim 1, comprising the steps of:
  a) stirring a suspension of Tigecycline in a suitable solvent at room temperature to form a suspension;
  b) adding hydrochloric acid to the suspension; and
  c) isolating crystalline form A of Tigecycline hydrochloride.

8. The process of preparing crystalline form A of Tigecycline hydrochloride according to claim 7, wherein the suitable solvent is selected from the group consisting of ketones, nitriles, esters, and ethers having a boiling point below about 120° C.

9. The process of preparing crystalline form A of Tigecycline hydrochloride according to claim 7, wherein the suitable solvent is selected from the group consisting of acetone, ethylmethylketone, acetonitrile, methylacetate, ethylacetate, isopropylacetate, tetrahydrofuran and 1,4-dioxane.

10. The process of preparing crystalline form A of Tigecycline hydrochloride according to claim 7, wherein the suitable solvent comprises acetonitrile.

11. The process of preparing crystalline form A of Tigecycline hydrochloride according to claim 7, wherein the solvent comprises a mixture of dimethylformamid and diethylether.

12. The process of preparing crystalline form A of Tigecycline hydrochloride according to claim 7, wherein the Tigecycline is slurried at a concentration of from 5 to 200 g/L.

13. The process of preparing crystalline form A of Tigecycline hydrochloride according to claim 7, wherein the Tigecycline is slurried at a concentration of from 10 to 50 g/L.

14. The process of preparing crystalline form A of Tigecycline hydrochloride according to claim 7, wherein the hydrochloric acid is added in step b) such that the ratio of Tigecycline to hydrochloric acid is about 0.9 to about 1.5 molar equivalents of hydrochloric acid to 1 molar equivalent of Tigecycline.

15. The process of preparing crystalline form A of Tigecycline hydrochloride according to claim 7, wherein the hydrochloric acid is added in step b) such that the ratio of Tigecycline to hydrochloric acid is about 1.0 to about 1.4 molar equivalents of hydrochloric acid to 1 molar equivalent of Tigecycline.

16. A process for the preparation of crystalline form A of Tigecycline hydrochloride as defined in claim 1, comprising the steps of:
    a) dissolving Tigecycline in a suitable solvent at a temperature ranging from room temperature to the boiling point of the used solvent to form a solution;
    b) adding hydrochloric acid to the solution of step a), wherein a precipitate forms to form a suspension;
    c) cooling down the suspension to room temperature or below; and
    d) isolating crystalline form A of Tigecycline hydrochloride.

17. The process of preparing crystalline form A of Tigecycline hydrochloride according to claim 16, wherein the suitable solvent is selected from the group consisting of ketones, nitriles, esters, and ethers having a boiling point below about 120° C.

18. The process of preparing crystalline form A of Tigecycline hydrochloride according to claim 16, wherein the suitable solvent is selected from the group consisting of acetone, ethylmethylketone, acetonitrile, methylacetate, ethylacetate, isopropylacetate, tetrahydrofuran and 1,4-dioxane.

19. The process of preparing crystalline form A of Tigecycline hydrochloride according to claim 16, wherein the suitable solvent comprises acetonitrile.

20. The process of preparing crystalline form A of Tigecycline hydrochloride according to claim 16, wherein the solvent comprise a mixture of dimethylformamide and diethylether.

21. The process of preparing crystalline form A of Tigecycline hydrochloride according to claim 16, wherein the Tigecycline is dissolved at a concentration of from 5 to 50 g/L.

22. The process of preparing crystalline form A of Tigecycline hydrochloride according to claim 16, wherein the Tigecycline is dissolved at a concentration of from 5 to 15 g/L.

23. The process of preparing crystalline form A of Tigecycline hydrochloride according to claim 16, wherein the hydrochloric acid is added in step b) such that the ratio of Tigecycline to hydrochloric acid is about 0.9 to about 1.5 molar equivalents of hydrochloric acid to 1 molar equivalent of Tigecycline.

24. The process of preparing crystalline form A of Tigecycline hydrochloride according to claim 16, wherein the hydrochloric acid is added in step b) such that the ratio of Tigecycline to hydrochloric acid is about 1.0 to about 1.4 molar equivalents of hydrochloric acid to 1 molar equivalent of Tigecycline.

25. A pharmaceutical composition formed from an effective amount of crystalline form A of Tigecycline hydrochloride as defined in claim 1.

26. A crystalline form B of Tigecycline hydrochloride having an X-ray powder diffraction pattern with peaks at 2-theta angles of 5.8°±0.2°, 7.0±0.2°, 9.1±0.2°, 9.7±0.2°, 14.1±0.2°, 15.5±0.2°, 17.3±0.2°, 18.3±0.2°, 19.6±0.2°, 22.4±0.2°, 25.5±0.2°, 27.1±0.2° and 28.5±0.2°.

27. The crystalline form B of Tigecycline hydrochloride according to claim 26 having an X-ray powder diffraction of FIG. 4.

28. The crystalline form B of Tigecycline hydrochloride according to claim 26 having an Infrared spectrum with peaks at wavenumbers of 3365±2 $cm^{-1}$, 3228±2 $cm^{-1}$, 1685±2 $cm^{-1}$, 1648±2 $cm^{-1}$, 1545±2 $cm^{-1}$, 1360±2 $cm^{-1}$, 1263±2 $cm^{-1}$, 1204±2 $cm^{-1}$ and 872±2 $cm^{-1}$.

29. The crystalline form B of Tigecycline hydrochloride according to claim 26 having an Infrared spectrum according to FIG. 5.

30. The crystalline form B of Tigecycline hydrochloride according to claim 26 having a differential scanning calorimetric curve of FIG. 6.

31. A process for the preparation of crystalline form B of Tigecycline hydrochloride as defined in claim 26, comprising the steps of:
    a) stirring a mixture of Tigecycline and methylenchloride;
    b) adding hydrochloric acid;
    c) stirring the mixture at room temperature or below to effect crystallization of crystalline form B of Tigecycline hydrochloride; and
    d) isolating crystalline form B of Tigecycline hydrochloride.

32. The process according to claim 31, wherein the hydrochloric acid is added in step b) such that the ratio of Tigecycline to hydrochloric acid is about 0.9 to about 1.5 molar equivalents of hydrochloric acid to 1 molar equivalent of Tigecycline.

33. The process according to claim 31, wherein the hydrochloric acid is added in step b) such that the ratio of Tigecycline to hydrochloric acid is about 1.0 to about 1.4 molar equivalents of hydrochloric acid to 1 molar equivalent of Tigecycline.

* * * * *